United States Patent [19]

Crook

[11] Patent Number: 5,330,477

[45] Date of Patent: Jul. 19, 1994

[54] APPARATUS AND METHOD FOR BONE FIXATION AND FUSION STIMULATION

[75] Inventor: David F. Crook, Garland, Tex.

[73] Assignee: AMEI Technologies Inc., Wilmington, Del.

[21] Appl. No.: 826,991

[22] Filed: Jan. 28, 1992

[51] Int. Cl.⁵ ................................ A61B 17/56
[52] U.S. Cl. ........................... 606/69; 606/71
[58] Field of Search ............ 606/2, 61, 77, 78, 64–71; 623/23, 24, 16, 17; 403/201.1; 600/13, 9

[56] References Cited

U.S. PATENT DOCUMENTS

| | | | |
|---|---|---|---|
| 3,344,792 | 10/1967 | Offner | 623/24 |
| 3,745,995 | 7/1973 | Kraus | 128/82.1 |
| 3,842,841 | 10/1974 | Brighton et al. | 128/419 R |
| 4,027,392 | 6/1977 | Sawyer | 433/201.1 |
| 4,436,684 | 3/1984 | White | 264/138 |
| 4,696,290 | 9/1987 | Steffee | 606/61 |
| 4,760,548 | 7/1988 | Baker et al. | 364/718 |
| 4,827,918 | 5/1989 | Olerud | 606/61 |
| 4,841,975 | 6/1989 | Woolson | 128/653 |
| 4,939,646 | 7/1990 | Essinger et al. | 364/413 |
| 4,955,908 | 9/1990 | Frey | 606/61 |
| 5,000,166 | 3/1991 | Karpf | 606/61 |
| 5,007,936 | 4/1991 | Woolson | 623/23 |
| 5,030,236 | 7/1991 | Dean | 623/16 |
| 5,108,395 | 4/1992 | Laurain | 606/61 |
| 5,123,898 | 6/1992 | Liboff et al. | 600/13 |

FOREIGN PATENT DOCUMENTS 2254304  7/1975  France ........................ 606/61

OTHER PUBLICATIONS

"3D Imaging in Medicine", J. K. Udupa and G. T. Herman, CRC Press, 1991.

Primary Examiner—Michael A. Brown
Attorney, Agent, or Firm—Baker & Botts

[57] ABSTRACT

Apparatus and a method for promoting the healing of a bone having a fracture site or fusion site is provided. The apparatus includes a brace coupled to the site and adapted for stabilizing the site. Firmly coupled to the brace is an electronic circuit emitting an energy for stimulating the healing of the site, where the brace and the electronic circuit form substantially an integral unit.

31 Claims, 2 Drawing Sheets

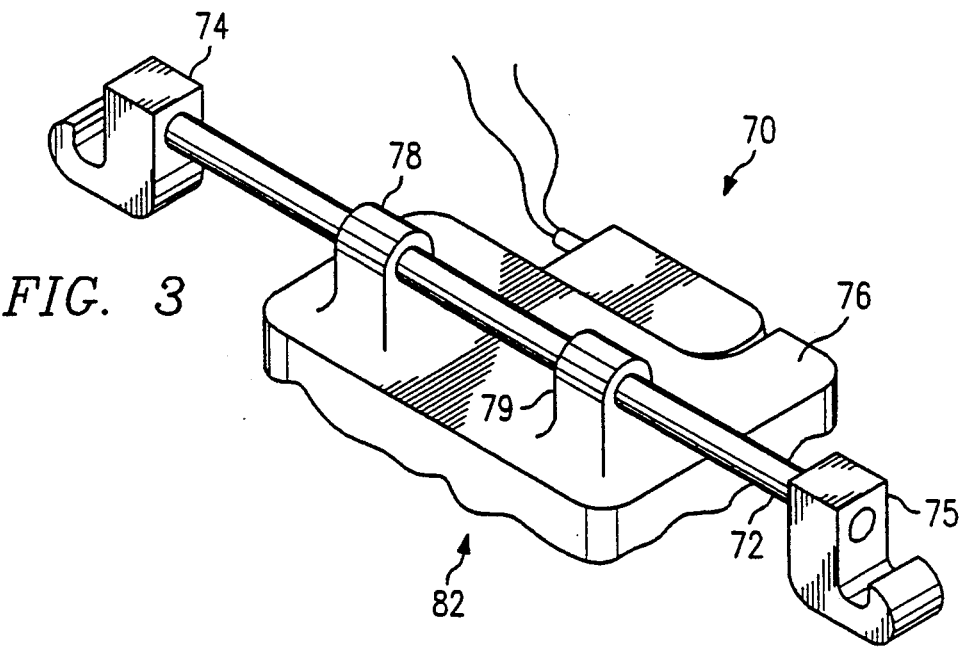
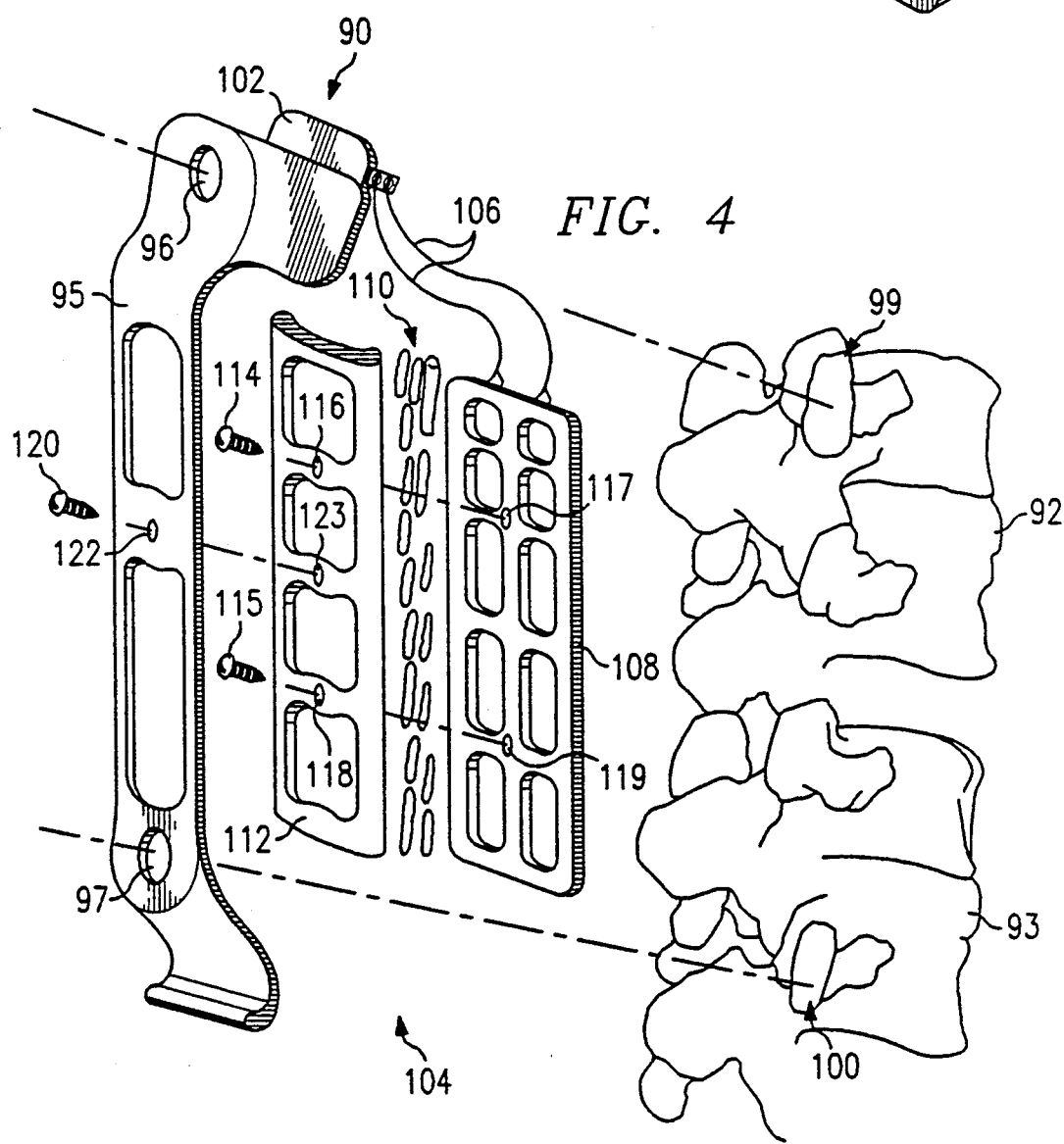

APPARATUS AND METHOD FOR BONE FIXATION AND FUSION STIMULATION

CROSS-REFERENCE TO RELATED APPLICATIONS

This application is related to U.S. application serial No. 07/827,002 filed Jan. 28, 1993 by David F. Crook and entitled "Apparatus For Distributed Bone Growth Stimulation", pending.

TECHNICAL FIELD OF THE INVENTION

This invention relates in general to the field of medical devices. More particularly, the present invention relates to apparatus and a method for stimulating bone growth and fusion while providing local stability.

BACKGROUND OF THE INVENTION

The miniaturization of electronic circuits prompted revolutionary advances in many areas of our lives. Some prominent examples range from lap top computers and pocket televisions to global positioning systems and prostheses that provide users with sensory feedback. The advances in electronics have also inspired research and development in the area of orthopedic bone growth stimulation, including the promotion of spinal fusion and healing. This is typically done by implanting electrical current generators in the vicinity of a bone fracture in a patient's body to create a DC electric current around the bone fracture. Studies have shown an improved rate of bone growth and fusion when the fractured bone is stimulated in this manner. Other promising stimulation methods include the use of transmitting ultrasound waves through the fracture site.

In addition to bone growth stimulation as outlined above, electronics implanted in the body may also play a role in patient health monitoring. For example, the progress of bone growth may be determined by measuring the amount of electrical resistance of the bone. It is also contemplated that ultrasound imaging is achievable by implanting ultrasound transmitters and receivers at opposed sites and aimed at the locality of interest. A more detailed description of such an ultrasound imaging system may also be found in the above-identified related patent applications.

Conventional methods of implanting electronic circuits, however, give rise to the disadvantage of possible migration of the electrical components, including electronic circuit packages, electrodes and battery packs causing potential shorting of device output. Also, because fracture and fusion sites are mechanically unstable it is common medical practice to provide internal stabilization. Therefore, a need has arisen for apparatus and a method for providing bone growth and fusion stimulation while stabilizing the fracture or fusion site.

SUMMARY OF THE INVENTION

In accordance with the present invention, apparatus and a method for bone fixation and stimulation are provided which substantially eliminate or reduce disadvantages and problems associated with prior applications.

In one aspect of the present invention, apparatus for promoting the healing of a bone having a fusion site or fracture site is provided. The apparatus includes a brace coupled to the bone and adapted for stabilizing the site. Firmly coupled to the brace is an electronic circuit emitting an energy for stimulating the healing of the bone, where the brace and the electronic circuit form substantially an integral unit. The bone injury may be traumatically or surgically induced.

In another aspect of the present invention, a method for promoting the healing of a bone having a fracture is provided. The method includes the steps of affixing a brace adapted for stabilizing the bone fracture to the bone, and implanting an electronic circuit in the brace. The electronic circuit and the brace are constructed to form substantially an integral unit. An energy is emitted to stimulate the healing of the bone.

An important technical advantage of the present invention provides for a substantially integral device which performs both the function of injury site stabilization and the function of providing stimulation to promote healing.

Another important technical advantage of the present invention provides for a device that is constructable from parts storable in a computer aided design library, so that the device may perform both the function of stabilizing the injury site and the functions of, for example, healing monitoring, pain control, telemetry, and electric field stimulation or ultrasound stimulation.

Yet another important technical advantage provides for a means of implanting an electronic circuit performing specific functions in a human body and securing it to a bone.

BRIEF DESCRIPTION OF THE DRAWINGS

For a better understanding of the present invention, reference may be made to the accompanying drawings, in which:

FIG. 3 is a perspective view of yet another preferred embodiment of the present invention; and FIG. 4 is an exploded view of yet another embodiment of the present invention.

DETAILED DESCRIPTION OF THE INVENTION

Figure 1:
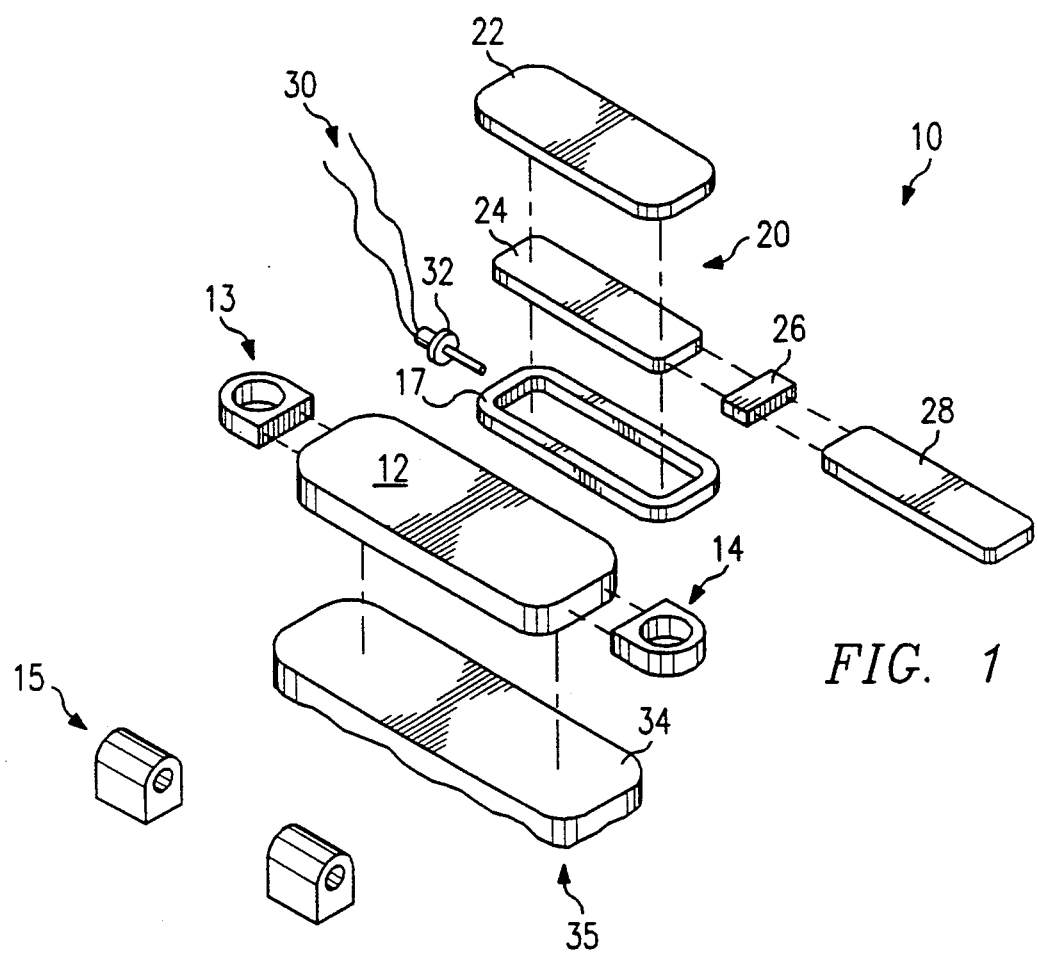
FIG. 1 is an exploded view of one preferred embodiment of the present invention.

With reference to the drawings, FIG. 1 illustrates an exploded view of one embodiment of the apparatus for bone fixation and stimulation, indicated generally at 10 and constructed according to the teaching of the present invention. The embodiment 10 of the present invention comprises parts and optional parts, the designs of which may be stored in a computer aided design (CAD) library (not shown). The parts are selectable from the CAD library by a physician or practitioner in accordance with the predefined needs of the patient. For example, if it is determined that an electric field stimulation in combination with a resistance reading and telemetry is desired for optimal healing promotion and monitoring for a particular patient, then apparatus 10 may be constructed with those parts selected from the library which perform these functions.

Apparatus 10 comprises a base plate 12, which includes fixation means 13 and 14 which provide firm coupling between base plate 12 and the underlying bone (not shown). Fixation means 13 and 14 may include openings, lying in the same plane as base plate 12 or in any plane of orientation, for receiving fasteners which secure base plate 12 to the underlying bone. The openings in fixation means 13 and 14 may be formed integral to base plate 12 or be constructed independently and then attached to base plate 12, as shown. Alternatively, apparatus 10 may be constructed by a stereolithography method, so that all selected parts are fashioned integrally from a single piece of raw material, such as implantable grade titanium, stainless steels, cobalt chrome steels, or appropriate plastics, ceramics or carbon fibre composites.

Alternatively, fixation means 13 and 14 may include means 15 for accepting a rod (an example of which is shown in FIG. 3) for fastening apparatus 10 to the underlying bone structure. This manner of stabilization is especially suited to providing fixation for injured spinal columns.

Onto base plate 12, an electronic module housing 17 may be formed which encloses an electronic module 20, along with a cover plate 22. Ideally, the inner cavity of housing 17 follows the outer contours of electronic module 20 closely and without substantial unused space. It is also preferable that electronic module 20 includes an insulative housing 24 which houses the electronic circuitry (not shown). In cases in which more than one electronic module is required, an interconnect device 26 may be used to couple electronic module 20 with an additional module 28, for example. Housing 17 and cover plate 22 may be expanded accordingly to accommodate the additional electronic module 28 and interconnect device 26. Additional parts, electrodes 30 for delivering the electric energy to the bone structure, for example, are provided. Electrodes 30 are connectable to electronic module 20 by a connector 32 that may have a threaded coupling with housing 17.

Apparatus 10 is shown in an exploded view in FIG. 1 to better display each independent part. However, once the parts deemed desirable for a specific application are selected, the resultant apparatus 10 is preferably of an integral construction. For example, all parts including fastening means 13, 14 or 15, base plate 12, and housing 17 (except electronic modules 20 and 28, module interconnector 26 and cover plate 22) may be constructed by forming and/or molding a single piece of material. Additionally, an interface plate 34 which may be formed integral with base plate 12 is provided. A surface 35 of interface plate 34 may have been prepared by rastographic data gathering, computer aided design, and stereo- lithographic modeling, so that the surface contour thereof is an inverse image of the bone surface to which apparatus 10 is to be affixed. In this manner, an intimate mating surface is provided to ensure substantially non-slippage and non-migration of apparatus 10 with respect to the underlying bone structure.

Figure 2:
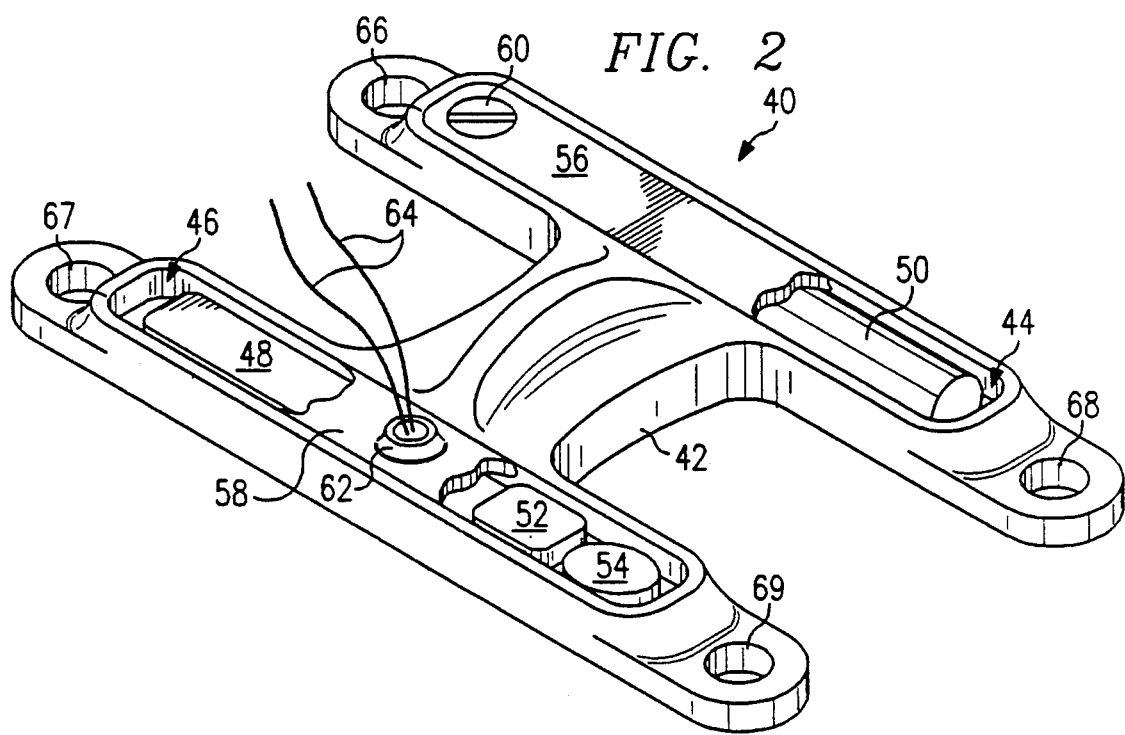
FIG. 2 is a perspective view of another preferred embodiment of the present invention, portions of which are cut away to provide a view of the electronic modules.

Referring to FIG. 2 for an alternate embodiment of the present invention, a perspective view of a generally H-shaped apparatus 40 for bone fixation and stimulation is shown. Apparatus 40 comprises a generally H-shaped brace structure 42 having cavities 44 and 46 for housing electronic modules 48-52 that perform, for example, bone stimulation, healing monitoring, telemetry, pain control and other functions. As discussed above, apparatus 40 can be tailored to encompass electronic module functions deemed necessary for a particular patient. In addition, a battery 54 may be included to provide the necessary electrical power to electronic modules 48-52. Cavities 44 and 46 are enclosed by cover plates 56 and 58, which may be secured by fasteners 60 or may be welded to form a substantially air-tight seal. Additionally, cover plates 56 and 58 may have openings 62 to allow electrode wires 64 to pass through, for example. Apparatus 40 may be fastened to the injured bone site by applying fasteners (not shown), such as bolts or screws and the like through openings 66-69.

Referring to FIG. 3, yet another embodiment of the present invention is shown. Apparatus 70 employs a rod fixation method, which uses a rod 72 with hook-like structures 74 and 75 at each respective end. Hook-like structures 74 and 75 are designed to be hooked onto certain features of the vertebrae in the spinal column in order to firmly secure apparatus 70 at or near the site of injury and to stabilize an injured vertebra or disc. Rod 72 is attached to a base plate 76 by inserting it through saddle-like structures 78 and 79, which are either firmly attached to base plate 76 or formed integrally therewith as one unit. Preferably, base plate 76 has a surface 82 that substantially conforms to the features of the injured bone to which apparatus 70 is to be affixed. As mentioned above, surface 82 may be constructed by way of rastographic data gathering, computer aided design and stereolithographic modeling.

Referring to FIG. 4, where an exploded view of yet another embodiment of the present invention is shown. Apparatus 90, as shown, is constructed to provide fixation and primarily stimulation to an injury site located between two vertebrae 92 and 93 on a spinal column. The injury may be, for example, a segmental instability which requires vertebrae 92 and 93 to remain fixed with respect to one another while fusion healing takes place.

Apparatus 90 comprises a fixation brace 95 shaped and contoured to follow closely the site of attachment on the spine. The contouring may be achieved by the rastographic data gathering, computer aided design and stereolithographic method described above, with the objective of realizing a brace which is custom made to fit unique fixation sites of individual patients. Brace 95, as shown in FIG. 4, is elongated and has two ends. At both ends, holes 96 and 97 are provided to receive fasteners, such as bolts or screws and the like (not shown) which fasten apparatus 90 to sites 99 and 100 on vertebrae 92 and 93, respectively. Note that other fastening means, such as the rod arrangement shown in FIG. 3, are also applicable in this embodiment.

Attached to brace 95 is an electronic module 102. Electronic module 102 may perform a myriad of functions including bone fusion stimulation, telemetry, fusion monitoring, and the like as described above. However, in the present embodiment, a field distribution device 104 is provided to improve the operation of electric field stimulation. A pair of electrode wires 106 extend from electronic module 102 and are coupled to a mesh electrode frame 108. Mesh electrode frame 108 is constructed of a substantially conductive and generally flexible material. It comprises a mesh frame that offer improved distribution of electromagnetic energy at and surrounding the injury site, and thus promotes an increased rate of healing.

On top of mesh electrode frame 108 is overlaid bone fragments or bone graft 110, and a bone graft retainer 112. Bone graft 110 is thus sandwiched between mesh electrode frame 108 and retainer 112 and held together by fasteners 114 and 115. Fasteners 114 and 115 are preferably screws which are inserted through threaded apertures 116-117 and 118-119, in fusion bone retainer 112 and mesh electrode frame 108, respectively. Field distribution device 104 is further coupled to brace 95 by a fastener, such as screw 120 which is adapted to be received by threaded apertures 122 and 123 in brace 95 and retainer 112, respectively.

In operation, electronic module 102 delivers an electric current to mesh electrode frame 108 via wire electrodes 106. Stimulated by the electric current in mesh electrode frame 108, fusion bones 110 grow together and fuse to the area between vertebrae 92 and 93 at an enhanced rate. When fusion is complete, brace 95 and retainer 112 along with electronic module 102 may be removed from the site.

Alternatively, a conductive mesh housing may be used to accommodate the fusion bones 110 and fastened to a brace 95. Upon healing of the bone fracture, brace 95 may be removed while leaving the mesh housing in place.

Although the present invention has been described in detail, it should be understood that various changes, substitutions and alterations can be made thereto without departing from the spirit and scope of the present invention as defined by the appended claims.

What is claimed is:

1. Apparatus for stimulating healing of and immobilizing a fracture or a fusion site of a bone, the bone having a bone surface with a bone contour, the apparatus comprising
   a substantially rigid plate having a surface for intimately mating with the bone surface;
   said surface having a preformed contour that is the inverse image of the bone contour;
   fastening means for securing said plate directly to the bone;
   an electronic-module housing secured to said plate; and
   an electronic module, removably disposed in said housing, having disposed therein an electronic circuit for generating and emitting an energy for stimulating the healing of the site.

2. The apparatus, as set forth in claim 1, wherein said housing defines a cavity adapted for receiving said electronic module.

3. The apparatus, as set forth in claim 2, further comprising a cover plate detachably mounted to said housing and over said cavity for enclosing said cavity.

4. The apparatus, as set forth in claim 1, further comprising a capsule for substantially enclosing and insulating said electronic module.

5. The apparatus, as set forth in claim 4, wherein said housing defines a cavity having a contour substantially matching that of said capsule, said cavity adapted for accommodating said capsule.

6. The apparatus, as set forth in claim 1, further comprising a battery affixed to said plate for supplying power to said electronic module.

7. The apparatus, as set forth in claim 6, wherein said defines a cavity adapted for accommodating said battery.

8. The apparatus, as set forth in claim 7, further comprising a cover plate for enclosing said cavity.

9. The apparatus, as set forth in claim 1, wherein said electronic circuit monitors a characteristic indicative of the progress of the healing of said site.

10. The apparatus, as set forth in claim 1, wherein said electronic circuit monitors a characteristic indicative of the status of the apparatus.

11. The apparatus, as set forth in claim 1, wherein said electronic module further comprises a transmitter for converting data into a radio frequency signal adapted for broadcasting.

12. The apparatus, as set forth in claim 1, wherein said emitted energy is an electric current.

13. The apparatus, as set froth in claim 1, wherein said emitted energy is ultrasound.

14. The apparatus, as set forth in claim 1, further comprising more than one electronic circuit said electronic circuits providing stimulating energy to promote the healing of the site, emitting diagnostic energy into the site, receiving said emitted diagnostic energy, and determining the state of health of the site.

15. The apparatus, as set forth in claim 1, wherein said fastening means comprises a fixation means.

16. The apparatus, as set forth in claim 15, further comprising screws for coupling said fixation means to the bone.

17. The apparatus, as set forth in claim 15, further comprising bolts for coupling said fixation means to the bone.

18. The apparatus, as set forth in claim 15, wherein said fastening means comprises a rod having a hook-like member on each end, said hook-like members adapted for hooking onto designated features of the site to secure said plate thereto.

19. A method for promoting the healing of a fracture or fusion site of a bone having a bone surface with a bone contour, the method comprising the steps of:
   providing a substantially rigid plate having a surface with a preformed contour that is the inverse image of the bone contour;
   affixing said plate directly to the bone for immobilizing the site such that said surface intimately mates with the bone surface:
   removably disposing an electronic module, having an electrode circuit, in a housing attached to said plate; and
   generating an energy signal with said electronic circuit to stimulate the healing of the site.

20. The method, as set forth in claim 19, further comprising the step of forming a cavity within said housing for receiving said electronic circuit.

21. The method, as set forth in claim 20, further comprising the step of substantially enclosing said cavity.

22. The method, as set forth in claim 19, further comprising the steps of encapsulating said electronic module and affixing said encapsulated electronic module within said housing.

23. The method, as set forth in claim 22, further comprising the step of providing a cavity having a contour substantially matching that of said capsule.

24. The method, as set forth in claim 19, further comprising the step of supplying power to said electronic circuit with a battery attached to said plate.

25. The method, as set forth in claim 19, further comprising the step of receiving said emitted energy with a receiver disposed within said housing.

26. The method, as set forth in claim 25, wherein said emitted energy receiving step comprises a step of receiving said energy having a characteristic indicative of the amount of healing in the site.

27. The method, as set forth in claim 26, further comprising the step of using a transmitter disposed within said housing for converting said received energy into a radio frequency signal adapted for broadcasting.

28. The method, as set forth in claim 19, wherein said energy emitting step comprises a step of emitting an electromagnetic energy.

29. The method, as set forth in claim 19, wherein said energy emitting step comprises a step of emitting an ultrasonic energy.

30. The method, as set forth in claim 19, further comprising the steps of emitting stimulating energy to promote the healing of the site, and emitting diagnostic energy into the site, receiving said emitted diagnostic energy, and determining the state of health of the site.

31. A method for healing a fracture or fusion site of a bone having a bone surface with a bone contour, the method comprising the steps of:

designing a plurality of electronic circuits adapted to perform a number of functions including emitting a stimulating energy, emitting a diagnostic energy, receiving said diagnostic energy, and broadcasting said received diagnostic energy;

designing a plurality of braces adapted for immobilizing an injured bone and accommodating said electronic circuits;

storing said braces and electronic circuit designs in a components library;

determining the need of a patient and the bone contour of the site;

selecting a brace and electronic circuits from said components library in response to said determination;

designing for said brace a surface having a contour the inverse image of the bone contour;

manufacturing a custom brace having said surface and said electronic circuits in response to said selection; and installing said custom brace and electronic circuits in said patient such that said surface intimately mates with said bone surface.

* * * * *

UNITED STATES PATENT AND TRADEMARK OFFICE
CERTIFICATE OF CORRECTION

PATENT NO. : 5,330,477
DATED : Jul. 19, 1994
INVENTOR(S) : Crook

It is certified that error appears in the above-identified patent and that said Letters Patent is hereby corrected as shown below:

| | |
|---|---|
| Column 5, Claim 1, Line 4 | After "comprising", insert --:--. |
| Column 5, Claim 7, Line 2 | Before "defines", insert --housing--. |
| Column 6, Claim 14, Line 2 | After "circuit", insert --,--. |
| Column 6, Claim 18, Line 1 | After "claim", delete "15" and insert --1--. |
| Column 6, Claim 19, Line 9 | After "surface", delete ":", and insert --;--. |
| Column 6, Claim 19, Line 11 | Delete "electrode", and insert --electronic--. |

Signed and Sealed this

Fifth Day of September, 1995

Attest:

BRUCE LEHMAN

*Attesting Officer*　　　*Commissioner of Patents and Trademarks*